United States Patent
Ray, II

(10) Patent No.: US 9,468,601 B2
(45) Date of Patent: Oct. 18, 2016

(54) DRY PHARMACEUTICAL COMPOSITIONS FOR TOPICAL DELIVERY OF ORAL MEDICATIONS, NASAL DELIVERY AND TO TREAT EAR DISORDERS

(71) Applicant: CMPD LICENSING LLC, Conroe, TX (US)

(72) Inventor: Jay Richard Ray, II, Conroe, TX (US)

(73) Assignee: CMPD LICENSING, LLC, Conroe, TX (US)

(*) Notice: Subject to any disclaimer, the term of this patent is extended or adjusted under 35 U.S.C. 154(b) by 0 days.

(21) Appl. No.: 14/797,860

(22) Filed: Jul. 13, 2015

(65) Prior Publication Data

US 2015/0313836 A1 Nov. 5, 2015

Related U.S. Application Data

(63) Continuation of application No. 13/920,903, filed on Jun. 18, 2013, now Pat. No. 9,078,853.

(51) Int. Cl.

| A61K 31/4196 | (2006.01) |
|---|---|
| A61K 31/42 | (2006.01) |
| A61K 31/505 | (2006.01) |
| A61K 31/56 | (2006.01) |
| A61K 9/00 | (2006.01) |
| A61K 38/14 | (2006.01) |
| A61K 31/351 | (2006.01) |
| A61K 31/4704 | (2006.01) |
| A61K 31/495 | (2006.01) |
| A61K 31/496 | (2006.01) |
| A61K 31/5383 | (2006.01) |
| A61K 31/575 | (2006.01) |
| A61K 31/7034 | (2006.01) |
| A61K 31/7048 | (2006.01) |
| A61K 31/7052 | (2006.01) |
| A61K 38/12 | (2006.01) |
| A61K 31/569 | (2006.01) |
| A61K 31/635 | (2006.01) |
| A61K 31/538 | (2006.01) |
| A61K 31/7036 | (2006.01) |
| A61K 31/47 | (2006.01) |
| A61K 38/13 | (2006.01) |

(52) U.S. Cl.
CPC ........... *A61K 9/0014* (2013.01); *A61K 9/0043* (2013.01); *A61K 9/0046* (2013.01); *A61K 9/0053* (2013.01); *A61K 31/351* (2013.01); *A61K 31/4196* (2013.01); *A61K 31/42* (2013.01); *A61K 31/47* (2013.01); *A61K 31/4704* (2013.01); *A61K 31/495* (2013.01); *A61K 31/496* (2013.01); *A61K 31/505* (2013.01); *A61K 31/538* (2013.01); *A61K 31/5383* (2013.01); *A61K 31/56* (2013.01); *A61K 31/569* (2013.01); *A61K 31/575* (2013.01); *A61K 31/635* (2013.01); *A61K 31/7034* (2013.01); *A61K 31/7036* (2013.01); *A61K 31/7048* (2013.01); *A61K 31/7052* (2013.01); *A61K 38/12* (2013.01); *A61K 38/13* (2013.01); *A61K 38/14* (2013.01)

(58) Field of Classification Search
None
See application file for complete search history.

(56) References Cited

U.S. PATENT DOCUMENTS

| 5,407,663 | A | 4/1995 | Eisen |
|---|---|---|---|
| 5,524,622 | A | 6/1996 | Wilson |
| 5,603,943 | A | 2/1997 | Yanagawa |
| 5,668,119 | A | 9/1997 | Medenica |
| 6,066,629 | A | 5/2000 | Moir et al. |
| 6,093,417 | A | 7/2000 | Petrus |
| 6,299,608 | B1 | 10/2001 | Solomon et al. |
| 8,084,445 | B2 | 12/2011 | Huq et al. |
| 8,129,364 | B2 | 3/2012 | Chaudry |
| 8,318,817 | B2 | 11/2012 | Lichter et al. |
| 8,338,648 | B2 | 12/2012 | Stock et al. |
| 8,663,663 | B1 | 3/2014 | Ray |
| 9,078,853 | B2 | 7/2015 | Ray |
| 2004/0235807 | A1 | 11/2004 | Weinrich et al. |
| 2005/0004002 | A1 | 1/2005 | Desai et al. |
| 2005/0053563 | A1 | 3/2005 | Manissier et al. |
| 2005/0148570 | A1 | 7/2005 | Huang et al. |
| 2006/0157507 | A1 | 7/2006 | Chang et al. |
| 2006/0228306 | A1 | 10/2006 | Lane |
| 2007/0037776 | A1 | 2/2007 | Richardson et al. |
| 2007/0065373 | A1 | 3/2007 | Morton et al. |
| 2007/0231274 | A1 | 10/2007 | Bhasin |
| 2007/0293460 | A1 | 12/2007 | Ray et al. |
| 2010/0183625 | A1 | 7/2010 | Sternlicht |

(Continued)

FOREIGN PATENT DOCUMENTS

| JP | 10-109928 | 4/1998 |
|---|---|---|
| WO | WO 2010/109434 | 9/2010 |

OTHER PUBLICATIONS

Patent Cooperation Treaty, "International Search Report and Written Opinion" U.S. International Searching Authority, by Officer Young, Lee W., in PCT Application No. PCT/US2014/041718, Document of 11 pages, dated Dec. 2, 2014.
Solares et al., "Treatment of chronic rhinosinusitis exacerbations due to methicillin-resistant *Staphylococcus aureus* with mupirocin irrigations," American Journal of Otolaryngology—Head and Neck Medicine and Surgery, 2006, vol. 27, pp. 161-165.

(Continued)

*Primary Examiner* — Jeffrey E Russel
(74) *Attorney, Agent, or Firm* — Akerman LLP

(57) ABSTRACT

In one aspect, a dry formulation for the effective administration of multiple medications simultaneously for one or more ailments may be provided. The dry formulations include one or more of the following actives in combination with pharmaceutically acceptable excipients or additives: a) at least one antibiotic; b) at least one anti-inflammatory steroid; and c) at least one antifungal agent.

16 Claims, No Drawings

(56) References Cited

U.S. PATENT DOCUMENTS

| | | |
|---|---|---|
| 2011/0081411 A1 | 4/2011 | Perrett et al. |
| 2011/0160118 A1 | 6/2011 | Podolsky |
| 2011/0224176 A1 | 9/2011 | Dobak et al. |
| 2012/0132204 A1 | 5/2012 | Lucking et al. |
| 2012/0164080 A1 | 6/2012 | Hill et al. |
| 2013/0149345 A1 | 6/2013 | Lipp et al. |
| 2014/0371179 A1 | 12/2014 | Simmons |

OTHER PUBLICATIONS

Uren et al., Nasal Lavage With Mupirocin for the Treatment of Surgically Recalcitrant Chronic Rhinosinusitis, Laryngocope, 2008, vol. 118, pp. 1677-1680.
Sankar et al., "Local drug delivery for oral mucosal diseases: challenges and opportunities," Oral Diseases, 2011, vol. 17, Supplement 1, pp. 73-84.
Arora R, et al. (2011) Voriconazole versus natamycin as primary treatment in fungal corneal ulcers. Clin Experiment Ophthalmol. 39(5):434-440.
Aykut S, et al. (2010) Mupirocin application at the exit site in peritoneal dialysis patients: five years of experience. Ren Fail. 32(3):356-361. (Abstract Only).
Bai T, et al. (2010) Short-term comparative study of the effects of preserved and unpreserved topical levofloxacin on the human ocular surface. Cutan Ocul Toxicol. 29(4):247-253. (Abstract Only).
Barikbin B, et al. (2009) Pimecrolimus 1% cream versus betamethasone 17-valerate 0.1% cream in the treatment of facial discoid lupus erythematosus: a double-blind, randomized pilot study. Clin Exp Dermatol. 34(7):776-780. (Abstract Only).
Barker GJ, et al. (1995) Oral care with vancomycin paste for reduction in incidence of alpha-hemolytic streptococcal sepsis. J Pediatr Hematol Oncol. 17(2):151-155. (Abstract Only).
Bassiri-Jahromi S, et al. (2012) A comparative evaluation of combination therapy of fluconazole 1% and urea 40% compared with fluconazole 1% alone in a nail lacquer for treatment of onychomycosis: therapeutic trial. J Dermatolog Treat. 23(6):453-456. (Abstract Only).
Bleecker ER, et al. (2012) Once-daily fluticasone furoate is efficacious in patients with symptomatic asthma on low-dose inhaled corticosteroids. Ann Allergy Asthma Immunol. 109(5):353-358. (Abstract Only).
Cagle G, et al. (1981-1982) Topical tobramycin and gentamicin sulfate in the treatment of ocular infections: multicenter study. Curr Eye Res. 1(9):523-534. (Abstract Only).
Camacho F, et al. (2002) Oral and topical L-phenylalanine, clobetasol propionate, and UVA/sunlight—a new study for the treatment of vitiligo. J Drugs Dermatol. 1(2):127-131. (Abstract Only).
Carr WW, et al. (2012) Comparison of intranasal azelastine to intranasal fluticasone propionate for symptom control in moderate-to-severe seasonal allergic rhinitis. Allergy Asthma Proc. 33(6):450-458. (Abstract Only).
Chang AL, et al. (2012) A randomized, double-blind, placebo-controlled, pilot study to assess the efficacy and safety of clindamycin 1.2% and tretinoin 0.025% combination gel for the treatment of acne rosacea over 12 weeks. J Drugs Dermatol. 11(3):333-339. (Abstract Only).
Cherian P, et al. (2013) Oral antibiotics versus topical decolonization to prevent surgical site infection after Mohs micrographic surgery—a randomized, controlled trial. Dermatol Surg. 39(10):1486-1493. (Abstract Only).
Chiambaretta F, et al. (2008) Tear concentrations of azithromycin following topical administration of a single dose of azithromycin 0.5%, 1.0%, and 1.5% eyedrops (T1225) in healthy volunteers. Eur J Ophthalmol. 18(1):13-20.
Claréus BW, et al. (2009) The DESIRE study—psoriasis patients' satisfaction with topical treatment using a fixed combination of calcipotriol and betamethasone dipropionate in daily clinical practice. Eur J Dermatol. 19(6):581-585. (Abstract Only).

Colin J, et al. (2003) Corneal penetration of levofloxacin into the human aqueous humour: a comparison with ciprofloxacin. Acta Ophthalmol Scand. 81(6):611-613.
Comstock TL, et al. (2012) Safety and tolerability of loteprednol etabonate 0.5% and tobramycin 0.3% ophthalmic suspension in pediatric subjects. Paediatr Drugs. 14(2):119-130.
Corradini C, et al. (2006) Amphotericin B and lysine acetylsalicylate in the combined treatment of nasal polyposis associated with mycotic infection. J Investig Allergol Clin Immunol. 16(3):188-193.
Dehghani AR, et al. (2009) Cefazolin-Gentamicin versus Vancomycin-Ceftazidime Eye Drops for Bacterial Corneal Ulcers;a Randomized Clinical Trial. J Ophthalmic Vis Res. 4(1):19-23.
Denis F, et al. (2008) Microbiological efficacy of 3-day treatment with azithromycin 1.5% eye-drops for purulent bacterial conjunctivitis. Eur J Ophthalmol. 18(6):858-868.
Dransfield MT, et al. (2013) Once-daily inhaled fluticasone furoate and vilanterol versus vilanterol only for prevention of exacerbations of COPD: two replicate double-blind, parallel-group, randomised controlled trials. Lancet Respir Med. 1(3):210-223. (Abstract Only).
du Bois RM, et al. (1999) Randomized trial of inhaled fluticasone propionate in chronic stable pulmonary sarcoidosis: a pilot study. Eur Respir J. 13(6):1345-1350. (Abstract Only).
Epstein JB, et al. (2002) Fluconazole mouthrinses for oral candidiasis in postirradiation, transplant, and other patients. Oral Surg Oral Med Oral Pathol Oral Radiol Endod. 93(6):671-675. (Abstract Only).
Fadlallah A, et al. (2012) Azithromycin 1.5% ophthalmic solution: efficacy and treatment modalities in chronic blepharitis. Arq Bras Oftalmol. 75(3):178-182.
Feldman SR, et al. (2009) Topical clobetasol propionate in the treatment of psoriasis: a review of newer formulations. Am J Clin Dermatol. 10(6):397-406.
Findlay A, et al. (2013) Increased peritoneal dialysis exit site infections using topical antiseptic polyhexamethylene biguanide compared to mupirocin: results of a safety interim analysis of an open-label prospective randomized study. Antimicrob Agents Chemother. 57(5):2026-2028.
Fluticasone Propionate—Accession No. DB00588. (2015) DrugBank. Available at http://www.drugbank.ca/drugs/DB00588. (17 pages).
Flynn PM, et al. (1995) Oropharyngeal candidiasis in immunocompromised children: a randomized, multicenter study of orally administered fluconazole suspension versus nystatin. The Multicenter Fluconazole Study Group. J Pediatr. 127(2):322-328. (Abstract Only).
Fowler PD, et al. (2002) A randomized double-blind study to compare the effects of nasal fluticasone and betamethasone on the hypothalamo-pituitary-adrenal axis and bone turnover in patients with nasal polyposis. Clin Otolaryngol Allied Sci. 27(6):489-493. (Abstract Only).
Gallenga PE, et al. (1999) Topical lomefloxacin 0.3% twice daily versus tobramycin 0.3% in acute bacterial conjunctivitis: A multicenter double-blind phase III study. Ophthalmologica. 213(4):250-257. (Abstract Only).
Giavina-Bianchi P, et al. (2008) Fluticasone furoate nasal spray in the treatment of allergic rhinitis. Ther Clin Risk Manag. 4(2):465-472.
Goldenberg D, et al. (2002) The use of otic powder in the treatment of acute external otitis. Am J Otolaryngol. 23(3):142-147. (Abstract Only).
Grossman J, et al. (1993) Fluticasone propionate aqueous nasal spray is safe and effective for children with seasonal allergic rhinitis. Pediatrics. 92(4):594-599. (Abstract Only).
Grove G, et al. (2013) Tolerability and irritation potential of four topical acne regimens in healthy subjects. J Drugs Dermatol. 12(6):644-649. (Abstract Only).
Howland WC 3rd, et al. (1996) The efficacy of fluticasone propionate aqueous nasal spray for allergic rhinitis and its relationship to topical effects. Clin Ther. 18(6):1106-1117. (Abstract Only).
Howland WC 3rd. (1996) Fluticasone propionate: topical or systemic effects? Clin Exp Allergy. 26 Suppl 3:18-22. (Abstract Only).
Jarratt MT, et al. (2012) Efficacy and safety of clindamycin-tretinoin gel versus clindamycin or tretinoin alone in acne vulgaris: a

(56) References Cited

OTHER PUBLICATIONS randomized, double-blind, vehicle-controlled study. J Drugs Dermatol. 11(3):318-326. (Abstract Only).
Keith PK. (2012) Fluticasone furoate nasal spray reduces symptoms of uncomplicated acute rhinosinusitis: a randomised placebo-controlled study. Prim Care Respir J. 21(3):267-275.
Khodaeiani E, et al. (2013) Topical 4% nicotinamide vs. 1% clindamycin in moderate inflammatory acne vulgaris. Int J Dermatol. 52(8):999-1004. (Abstract Only).
LaForce C, et al. (2013) Ocular safety of fluticasone furoate nasal spray in patients with perennial allergic rhinitis: a 2-year study. Ann Allergy Asthma Immunol. 111(1):45-50. (Abstract Only).
Lalitha P, et al. (2014) In vitro susceptibility of filamentous fungal isolates from a corneal ulcer clinical trial. Am J Ophthalmol. 157(2):318-326.
Mandy RA, et al. (2010) Topical amphotericin B and subconjunctival injection of fluconazole (combination therapy) versus topical amphotericin B (monotherapy) in treatment of keratomycosis. J Ocul Pharmacol Ther. 26(3):281-285. (Abstract Only).
Man LX, et al. (2013) The effect of intranasal fluticasone propionate irrigations on salivary cortisol, intraocular pressure, and posterior subcapsular cataracts in postsurgical chronic rhinosinusitis patients. Int Forum Allergy Rhinol. 3(12):953-957. (Abstract Only).
McHugh RC, et al. (2004) A topical azithromycin preparation for the treatment of acne vulgaris and rosacea. J Dermatolog Treat. 15(5):295-302. (Abstract Only).
Meltzer EO. (1997) The pharmacological basis for the treatment of perennial allergic rhinitis and non-allergic rhinitis with topical corticosteroids. Allergy. 52(36 Suppl):33-40.
Milgrom P, et al. (2009) Xylitol pediatric topical oral syrup to prevent dental caries: a double-blind randomized clinical trial of efficacy. Arch Pediatr Adolesc Med. 163(7):601-607.
Miño de Kaspar H, et al. (2008) A prospective randomized study to determine the efficacy of preoperative topical levofloxacin in reducing conjunctival bacterial flora. Am J Ophthalmol. 145(1):136-142.
Miura MS, et al. (2009) Topical clindamycin in post-adenotonsillectomy analgesia in children: a double-blind, randomized clinical trial. Otolaryngol Head Neck Surg. 141(4):509-515. (Abstract Only).
Muraki M, et al. (2009) Inhaled montelukast inhibits cysteinyl-leukotriene-induced bronchoconstriction in ovalbumin-sensitized guinea-pigs: the potential as a new asthma medication. Int Immunopharmacol. 9(11):1337-1341. (Abstract Only).
Nascimento FJ, et al. (2011) Topical betamethasone and hyaluronidase in the treatment of phimosis in boys: a double-blind, randomized, placebo-controlled trial. Int Braz J Urol. 37(3):314-319.
Nichols JJ, et al. (2012) Safety and efficacy of topical azithromycin ophthalmic solution 1.0% in the treatment of contact lens-related dry eye. Eye Contact Lens. 38(2):73-79.
NilFroushzadeh MA, et al. (2009) Clindamycin lotion alone versus combination lotion of clindamycin phosphate plus tretinoin versus combination lotion of clindamycin phosphate plus salicylic acid in the topical treatment of mild to moderate acne vulgaris: a randomized control trial. Indian J Dermatol Venereol Leprol. 75(3):279-282.
O'Brien TP, et al. (1995) Efficacy of ofloxacin vs cefazolin and tobramycin in the therapy for bacterial keratitis. Report from the Bacterial Keratitis Study Research Group. Arch Ophthalmol. 113(10):1257-1265. (Abstract Only).
Omidvari S, et al. (2007) Topical betamethasone for prevention of radiation dermatitis. Indian J Dermatol Venereol Leprol. 73(3):209. (Abstract Only).
Panahi Y, et al. (2011) Doxepin cream vs betamethasone cream for treatment of chronic skin lesions due to sulfur mustard. Skinmed. 9(3):152-158. (Abstract Only).
Panda A, et al. (1996) Topical fluconazole therapy of Candida keratitis. Cornea. 15(4):373-375. (Abstract Only).
Pazoki-Toroudi H, et al. (2011) Combination of azelaic acid 5% and clindamycin 2% for the treatment of acne vulgaris. Cutan Ocul Toxicol. 30(4):286-291. (Abstract Only).
Philip G, et al. (2010) A phase I randomized, placebo-controlled, dose-exploration study of single-dose inhaled montelukast in patients with chronic asthma. J Asthma. 47(10):1078-1084. (Abstract Only).
Philip G, et al. (2011) The efficacy and tolerability of inhaled montelukast plus inhaled mometasone compared with mometasone alone in patients with chronic asthma. J Asthma. 48(5):495-502. (Abstract Only).
Pradeep AR, et al. (2008) Clinical and microbiologic effects of subgingivally delivered 0.5% azithromycin in the treatment of chronic periodontitis. J Periodontol. 79(11):2125-2135. (Abstract Only).
Prevost NM, et al. (2007) Palliative treatment of fingernail lichen planus. J Drugs Dermatol. 6(2):202-204. (Abstract Only).
Saraceno R, et al. (2014) Efficacy and maintenance strategies of two-compound formulation calcipotriol and betamethasone dipropionate gel (Xamiol® gel) in the treatment of scalp psoriasis: results from a study in 885 patients. J Dermatolog Treat. 25(1):30-33. (Abstract Only).
Scadding GK. (2000) Other anti-inflammatory uses of intranasal corticosteroids in upper respiratory inflammatory diseases. Allergy. 55 Suppl 62:19-23.
Scheinfeld N. (2008) Pruritic urticarial papules and plaques of pregnancy wholly abated with one week twice daily application of fluticasone propionate lotion: a case report and review of the literature. Dermatol Online J. 14(11):4.
Sharma N, et al. (2013) Comparative evaluation of topical versus intrastromal voriconazole as an adjunct to natamycin in recalcitrant fungal keratitis. Ophthalmology. 120(4):677-681.
Ship JA, et al. (2007) Safety and effectiveness of topical dry mouth products containing olive oil, betaine, and xylitol in reducing xerostomia for polypharmacy-induced dry mouth. J Oral Rehabil. 34(10):724-732.
Sholapurkar AA, et al. (2009) Comparison of efficacy of fluconazole mouthrinse and clotrimazole mouthpaint in the treatment of oral candidiasis. Aust Dent J. 54(4):341-346.
Silverman M, et al. (2003) Episodic viral wheeze in preschool children: effect of topical nasal corticosteroid prophylaxis. Thorax. 58(5):431-434.
Tai YJ, et al. (2013) Nasal carriage of *Staphylococcus aureus* in patients undergoing Mohs micrographic surgery is an important risk factor for postoperative surgical site infection: a prospective randomised study. Australas J Dermatol. 54(2):109-114. (Abstract Only).
Thorild I, et al. (2006) Caries in 4-year-old children after maternal chewing of gums containing combinations of xylitol, sorbitol, chlorhexidine and fluoride. Eur Arch Paediatr Dent. 7(4):241-245. (Abstract Only).
Ulff E, et al. (2013) A potent steroid cream is superior to emollients in reducing acute radiation dermatitis in breast cancer patients treated with adjuvant radiotherapy. A randomised study of betamethasone versus two moisturizing creams. Radiother Oncol. 108(2):287-292. (Abstract Only).
Uren B, et al. (2008) Nasal lavage with mupirocin for the treatment of surgically recalcitrant chronic rhinosinusitis. Laryngoscope. 118(9):1677-1680.
Vander Salm TJ, et al. (1989) Reduction of sternal infection by application of topical vancomycin. J Thorac Cardiovasc Surg. 98(4):618-622. (Abstract Only).
Vural C, et al. (2003) The effect of topical fluticasone on nasal nitric oxide levels in a patient with allergic rhinitis. Ear Nose Throat J. 82(8):592-597. (Abstract Only).
Wu W, et al. (2013) An integrated analysis of the efficacy of fluticasone furoate nasal spray versus placebo on the nasal symptoms of perennial allergic rhinitis. Allergy Asthma Proc. 34(3):283-291. (Abstract Only).
Yactayo-Miranda Y, et al. (2009) A prospective study determining the efficacy of topical 0.5% levofloxacin on bacterial flora of patients with chronic blepharoconjunctivitis. Graefes Arch Clin Exp Ophthalmol. 247(7):993-998.

(56) References Cited

OTHER PUBLICATIONS

Yim SM, et al. (2010) Study to compare the efficacy and safety of fluconazole cream with flutrimazole cream in the treatment of superficial mycosis: a multicentre, randomised, double-blind, phase III trial. Mycoses. 53(6):522-529. (Abstract Only).
Yoon KC, et al. (2007) Therapeutic effect of intracameral amphotericin B injection in the treatment of fungal keratitis. Cornea. 6(7):814-818. (Abstract Only).
Restriction Requirement issued Aug. 22, 2013 for U.S. Appl. No. 13/920,903, filed Jun. 18, 2013 (Inventor—Jay Richard Jay, II) (8 pages).
Examiner Interview Summary issued Sep. 16, 2013 for U.S. Appl. No. 13/920,903, filed Jun. 18, 2013 (Inventor—Jay Richard Jay, II) (2 pages).
Response to Restriction Requirement filed Sep. 23, 2013 for U.S. Appl. No. 13/920,903, filed Jun. 18, 2013 (Inventor—Jay Richard Jay, II) (3 pages).
Non-Final Office Action issued Dec. 2, 2013 for U.S. Appl. No. 13/920,903, filed Jun. 18, 2013 (Inventor—Jay Richard Jay, II) (12 pages).
Response filed May 2, 2014 for U.S. Appl. No. 13/920,903, filed Jun. 18, 2013 (Inventor—Jay Richard Jay, II) (15 pages).
Final Office Action issued May 14, 2014 for U.S. Appl. No. 13/920,903, filed Jun. 18, 2013 (Inventor—Jay Richard Jay, II) (15 pages).
Examiner Interview Summary issued Aug. 26, 2014 for U.S. Appl. No. 13/920,903, filed Jun. 18, 2013 (Inventor—Jay Richard Jay, II) (2 pages).
Response filed Sep. 15, 2014 for U.S. Appl. No. 13/920,903, filed Jun. 18, 2013 (Inventor—Jay Richard Jay, II) (12 pages).
Non-Final Office Action issued Sep. 29, 2014 for U.S. Appl. No. 13/920,903, filed Jun. 18, 2013 (Inventor—Jay Richard Jay, II) (16 pages).
Response filed Dec. 29, 2014 for U.S. Appl. No. 13/920,903, filed Jun. 18, 2013 (Inventor—Jay Richard Jay, II) (7 pages).
Non-Final Office Action issued Jan. 27, 2015 for U.S. Appl. No. 13/920,903, filed Jun. 18, 2013 (Inventor—Jay Richard Jay, II) (8 pages).
Response filed Apr. 15, 2015 for U.S. Appl. No. 13/920,903, filed Jun. 18, 2013 (Inventor—Jay Richard Jay, II) (8 pages).
Final Office Action issued May 5, 2015 for U.S. Appl. No. 13/920,903, filed Jun. 18, 2013 (Inventor—Jay Richard Jay, II) (8 pages).
Response filed May 8, 2015 for U.S. Appl. No. 13/920,903, filed Jun. 18, 2013 (Inventor—Jay Richard Jay, II) (5 pages).
Notice of Allowance issued May 14, 2015 for U.S. Appl. No. 13/920,903, filed Jun. 18, 2013 (Inventor—Jay Richard Jay, II) (5 pages).
Communication re: Application Data Sheet filed May 21, 2015 for U.S. Appl. No. 13/920,903, filed Jun. 18, 2013 (Inventor—Jay Richard Jay, II) (6 pages).
Issue Notification issued Jun. 24, 2015 for U.S. Appl. No. 13/920,903, filed Jun. 18, 2013 (Inventor—Jay Richard Jay, II) (6 pages).
International Preliminary Report on Patentability issued Dec. 22, 2015 for PCT Application No. PCT/US2014/041718 filed Jun. 10, 2014 (published as WO 2014/204718 on Dec. 24, 2014) (Applicant—JCDS Holdings, LLC) (11 pages).

DRY PHARMACEUTICAL COMPOSITIONS FOR TOPICAL DELIVERY OF ORAL MEDICATIONS, NASAL DELIVERY AND TO TREAT EAR DISORDERS

CROSS-REFERENCE TO RELATED APPLICATIONS

This patent application is a continuation of U.S. patent application Ser. No. 13/920,903, filed Jun. 18, 2013, the entirety of which is incorporated herein by reference.

FIELD OF THE INVENTION

The present application relates to compounded therapies. In particular, the present application relates to compositions for compounded therapy and methods of compounding medications.

BACKGROUND

The need for effective therapeutic treatment of patients has resulted in the development of a variety of pharmaceutical composition delivery techniques. Administration of a drug or drug combination in form of a solution or a suspension is often desirable. Degradation of active agents can often occur in solutions or suspensions. As a result, many pharmaceutical formulations are restricted in the manner of their delivery, which may make them unsuitable for young children and other patients. Some solution or suspension formulations must be administered within minutes after opening the formulation's container, and any unused portion must be discarded after this time. Other formulations must be administered with a carrier, for example a small selection of soft foods. Such restrictions can lead to reduced patient compliance as well as wasted medication.

In other cases, although a particular drug may be chemically stable in water, liquid formulations such as aqueous solutions and suspensions for oral administration are not used because of the unpalatatability of the particular drug. Unpalatable drugs which are carried in aqueous media are tasted almost immediately upon ingestion and produce an unpleasant taste or after-taste. For example, the antibiotics clarithromycin and erythromycin are valuable therapeutic agents for treating infections and are somewhat unpalatable.

Additional problems resulting in poor shelf life which can occur in liquid formulations include particle agglomeration, stratification, and caking upon standing.

There is thus a need in the pharmaceutical formulation arts for stable drug formulations which can be administered in the form of an aqueous solution or suspension.

SUMMARY

In one embodiment, the invention provides a dry formulation comprising one or more of the following actives in combination with pharmaceutically acceptable excipients or additives: a) at least one antibiotic; b) at least one anti-inflammatory steroid; and c) at least one antifungal agent. Any or all of the actives can be included. The dry formulation can be formulated in any suitable form, such as a capsule. Pharmaceutically acceptable excipients or additives may be included and comprise at least one solvent, at least one emollient, at least one humectant, at least one preservative, and at least one emulsifier; and optionally including an acid, base, or buffering agent to adjust the pH; and include. In some embodiments, the pharmaceutically acceptable excipients or additives include a base for use in pharmaceutical compounding and manufacturing of topical preparations.

In some embodiments, the dry formulation does not contain an antihistamine.

In another embodiment, the dry formulation comprises one or more of the following actives in combination with pharmaceutically acceptable excipients or additives: a) at least one leukotriene receptor antagonist; b) at least one anti-inflammatory steroid; and c) at least one non-sedative antihistamine.

In some embodiments, the dry formulation is stable for 180 days.

Specific combinations of active ingredients include 5% azithromycin, 1.5% fluticasone, and 1.5% fluconazole; 8% sulfamethoxazole, 5% trimethoprim, 1.5% fluticasone, and 1.5% fluconazole; 12.8% levofloxacin hemihydrate, 1.5% fluticasone, and 1.5% fluconazole; 1.5% fluticasone and 1.5% fluconazole; 1.5% fluticasone.

Other specific combinations of active ingredients include 12.8% levofloxacin hemihydrate, 10% mupirocin, 1.5% fluticasone, and 5% itraconazole; 12.8% levofloxacin hemihydrate, 1.5% fluticasone, and 5% itraconazole; 12.8% levofloxacin hemihydrate, 1.5% fluticasone, and 1% amphotericin B; 16% tobramycin, 1.5% fluticasone, and 5% itraconazole; 16% tobramycin, 1.5% fluticasone, and 1% amphotericin B; 10% mupirocin, 1.5% fluticasone, and 5% itraconazole; 10% mupirocin, 1.5% fluticasone, and 1% amphotericin B; 5.15% vancomycin hydrochloride, 1.5% fluticasone, and 5% itraconazole; 5.15% vancomycin hydrochloride, 1.5% fluticasone, and 1% amphotericin B; 16% tobramycin, 20% mupirocin; 1.5% fluticasone and 1% amphotericin B; 1.5% fluticasone and 5% itraconazole.

Other specific combinations of active ingredients include 0.3% montelukast, 1.5% fluticasone, 0.2% levocetirizine dihydrochloride; 5.15% vancomycin hydrochloride, 20% mupirocin.

In other embodiments, methods of preparing administrable formulations from the dry formulation are provided. In one embodiment, the invention provides methods of preparing an orally administrable formulation comprising forming the dry formulations into an oral rinse or an oral solution. The oral formulations so prepared are also within the scope of the invention.

In another embodiment, the invention provides methods of preparing an intranasally administrable formulation comprising forming the dry formulations into a nasal solution or suspension with a diluent suitable for intranasal delivery of active ingredients. The formulations so prepared are also within the scope of the invention.

In another embodiment, the invention provides methods of preparing a formulation for aural administration comprising forming the dry formulations into a solution or suspension with a diluent suitable for otic delivery of active ingredients. The formulations so prepared are also included in the scope of the invention.

The oral rinse may include diphenhydramine, aluminium hydroxide, magnesium hydroxide, simethicone, an antiviral agent, such as acyclovir, a local anesthetic such as lidocaine, and the orally administrable formulations obtained by the methods.

Other methods include methods for treating inflammatory, ulcerative and painful conditions of mucosal surfaces of the upper alimentary canal of a mammal comprising administering the orally administrable formulation to a mammal, such as a human. The orally administrable formulation may an oral rinse in which the method comprises (1) swishing the oral rinse formulation; and (2) expectorating the oral rinse formulation. In other embodiments, the orally administrable formulation is an oral solution and the method comprises (1) swishing the oral solution; and (2) swallowing the oral solution.

Inflammatory, ulcerative and painful conditions include mucositis, aphthous stomatitis, oral lichen planus, eosinophilic esophogitis, an ulcer, erythema migrans, a condition resulting from gingivitis or a tooth extraction, antineoplastic therapy, such as radiation therapy or chemotherapy, or in connection with a bacterial, viral, or fungal infection such as candidias and herpes labialis.

The intranasal formulation may be administered by methods such as inhalation, spraying, liquid stream lavage, nebulizing, or nasal irrigation. The administering may be to the sinus cavity or the lungs, for example. The formulation can be administered, for example, two or three times a day.

Also provided are other methods for treating inflammatory, ulcerative and painful conditions of the respiratory tract, respiratory airways or lungs of a mammal, such as a human, comprising administering to a mammal, such as a human, the intranasally administrable formulations. Such conditions include those caused by a bacterial, viral, or fungal infection, such as a pseudomonas infection or a MRSA infection. The condition can also include an upper respiratory tract infection lower respiratory tract infection, bronchiolitis, pneumonia, dyspnea, cough, (recurrent) wheezing and asthma.

Also provided are methods for treating inflammatory, ulcerative and painful conditions of the ear of a mammal, such a human, comprising administering to said mammal the formulations for aural administration. The formulation can be administered by instillation of the solution or suspension into the ear canal. The formulations can be administered, for example, up to three times a day.

The conditions include otitis externa, otitis media, otorrhea, acute mastoiditis, otosclerosis, otic pain, otic bleeding, otic inflammation, Lermoyez's syndrome, Meniere's disease, vestibular neuronitis, benign paroxysmal positional vertigo, herpes zoster oticus, Ramsay Hunt's syndrome, viral neuronitis, ganglionitis, geniculate herpes, labyrinthitis, purulent labyrinthitis, perilymph fistulas, presbycusis, drug-induced ototoxicity, acoustic neuromas, aerotitis media, infectious myringitis, bullous myringitis, squamous cell carcinoma, basal cell carcinoma, pre-cancerous otic conditions, nonchromaffin paragangliomas, chemodectomas, glomus jugulare tumors, glomus tympanicum tumors, perichondritis, aural eczematoid dermatitis, malignant external otitis, subperichondrial hematoma, ceruminomas, impacted cerumen, sebaceous cysts, osteomas, keloids, otalgia, tinnitus, vertigo, tympanic membrane infection, tympanitis, otic furuncles, petrositis, conductive and sensorineural hearing loss, epidural abscess, lateral sinus thrombosis, subdural empyema, otitic hydrocephalus, Dandy's syndrome, bullous myringitis, diffuse external otitis, foreign bodies, keratosis obturans, otic neoplasm, otomycosis, trauma, acute barotitis media, acute eustachian tube obstruction, postsurgical otalgia, cholesteatoma, infections related to an otic surgical procedure.

DETAILED DESCRIPTION

The present embodiments may relate dry compounded medications for treatment of various ailments, such as inflammatory, ulcerative and painful conditions of the mucosal surfaces of the upper alimentary canal of a mammal, the respiratory tract, respiratory airways or lungs of a mammal, and/or the ear of a mammal.

In one aspect, a dry formulation for the effective administration of multiple medications simultaneously for one or more ailments may be provided. The dry formulations include one or more of the following actives in combination with pharmaceutically acceptable excipients or additives: a) at least one antibiotic; b) at least one anti-inflammatory steroid; and c) at least one antifungal agent.

Formulations containing one or more of these ingredients are typically offered as aqueous solutions or suspension, or for topical applications, creams and gels which contain an aqueous component. Such aqueous-based formulations containing these active agents are often unstable, however. For example, with regard to formulations intended for oral use, the primary reason that many typically prescribed compounded "Magic Gargle" or "Magic Mouthwash" formulations have such an offensive taste is due to the degradation that happens to the medications themselves once mixed into a large volume bottle containing a host of different ingredients. These formulations are generally a compounded medication that has not been reviewed by the FDA for safety or efficacy, and there is no "standard" formula for such a compounded medication.

The dry formulations of medication described herein have an established shelf-life of 180 days from the date of compounding. At the time of administration, the patient simply mixes the dry formulation, e.g., the contents of a capsule, with the desired liquid. Since the medication is not mixed with the liquid until the time of administration, any offensive taste (due to degradation) is minimized. Further, since the medication is mixed at the time of administration, it retains its full potency.

Other advantage of the dry formulations include the ability to include a broad array of medications available for prescribing, such as antibiotics, antifungals, corticosteroids, antivirals, and local anesthetics. The dry formulations are also portable. For example, the patient can carry compounded capsules to be mixed at the time of administration with the desired liquid. This is particularly advantageous for travelers, as patient can simply travel with a small bottle of capsules and purchase the diluent liquid at his destination.

Finally, in that certain of the dry formulations are suitable for different types of administration. For example a composition containing azithromycin, fluticasone, and fluconazole, described below can be formed into a liquid for oral administration or administration to the ear. There is a manufacturing benefit in that a single dry formulation can be prepared, rather than two specific formulations.

In some embodiments, the dry formulations are encapsulated. They may be encapsulated in a unit dosage form. Encapsulation may be in the form of a capsule. In general, the capsule is a hard gelatin capsules filled with the dry powders by introducing the material into one section of the capsule and capping it with a second section. The capsule contents are removed for reconstitution into a liquid form for administration. Alternatively, the capsule can be of a type that dissolve in the reconstitution liquid to for a solution or suspension.

The dry formulation, in addition to the active ingredients, contains pharmaceutically acceptable excipients or additives. These may include, for example, solvents, surfactants, humectants, preservatives, flavorings, stabilizers (including antioxidants) colorants, and other additives used in preparations administered into the oral cavity, intranasally or via the ear.

Other medicinal agents may be added for purposes of alleviating other undesirable conditions in the mouth. Such agents may include, for example, anesthetics, analgesics, antibacterial agents, antiviral agents and emollients.

In some embodiments, the pharmaceutically acceptable excipients or additives include a base for use in pharmaceutical compounding and manufacturing of topical preparations. Such base compositions are known to those skilled in the art. In a preferred embodiment, the base is the PCCA base having the name LOXASPERSE. LOXASPERSE predominantly contains xylitol and polyethylene glycol (PEG).

In one embodiment, the dry formulation includes all of a) at least one antibiotic; b) at least one anti-inflammatory steroid; and c) at least one antifungal agent.

It should be understood that the compositions described herein which employ a base for use in pharmaceutical compounding and manufacturing of topical preparations, can be used for the preparation of compositions for topical administration for appropriate conditions, for example, keratitis, onychomycosis, Factors to be considered in choosing a particular anti-inflammatory agent include cost and absorption of the particular agent. Steroids particularly suggested for use in the method of the invention include, but are not limited to: triamcinolone and its derivatives (particularly the diacetate, hexacetonide, and acetonide), betamethasone and its derivatives (including particularly the dipropionate, benzoate, sodium phosphate, acetate, and valerate), dexamethasone and its derivatives (particularly the dipropionate and valerate), flunisolide, prednisone and its derivatives (particularly its acetate), prednisolone and its derivatives (particularly its acetate, sodium phosphate and tebutate), methylprednisolone and its derivatives (particularly its acetate and sodium succinate), fluocinolone and its derivatives (particularly the acetonide), diflorasone and its derivatives (particularly the diacetate), halcinonide, desoximetasone (desoxymethasone), diflucortolone and its derivatives (particularly the valerate), flucloronide (fluclorolone acetonide), fluocinonide, fluocortolone, fluprednidene and its derivatives (particularly the acetate), flurandrenolide (flurandrenolone), clobetasol and its derivatives (particularly the propionate), clobetasone and its derivatives (particularly the butyrate), alclometasone, flumethasone and its derivatives (particularly the pivalate), fluocortolone and its derivatives (particularly the hexanoate), amcinonide, beclometasone and its derivatives (particularly the dipropionate), fluticasone and its derivatives (particularly the propionate), difluprednate, prednicarbate, flurandrenolide, mometasone and desonide. Other preferred anti-inflammatory steroids are described herein.

Fluticasone is typically viewed safe in wide variety of patient populations due to low anticipated absorption in the in the gastrointestinal tract (GIT) and upper respiratory tract. Betamethasone is effective in treating inflammation in the oral cavity but does have an anticipated absorption rate of 40-60% based upon literature reviews in the GIT. Such absorption, if unwanted, would not be problematic with a swish/spit administration, although some absorption could conceivably still occur.

The effective concentration of drug will vary with the active agent used and mode of administration. Concentrations will generally fall within the 0.1% to 15% range. For example, for fluticasone and its derivatives the preferred concentration is from about 0.1% to about 10%, more preferably from about 0.5% to about 5%, and more preferably 1.5%.

The preferred antifungal agents include, but are not limited to, nystatin, clotrimazole, econazole, oxiconazole, ketoconazole, miconazole, ciclopirox, amphotericin B, and sulconazole, terbinafine, fluconazole, itraconazole, and amorolfine. amphotericin B, fluconazole, itraconazole nystatin, voriconazole and flucytosine are particularly preferred agents. Other preferred antifungal agents are described herein.

Fluconazole is typically viewed as safe in a wide variety of patient populations for a wide variety of reasons and is dosed orally (and swallowed) in pediatric patients.

Expected coverage for various antifungal agents is shown in Table 1 below.

TABLE 1

|  | Fluconazole | Itraconazole | Voriconazole | Amphotericin | Nystatin |
|---|---|---|---|---|---|
| *Aspergillus flavus* | yes | yes | yes | yes |  |
| *Aspergillus fumigatus* | yes | yes | yes | yes |  |
| *Aspergillus niger* |  |  | yes | yes |  |
| *Aspergillus terreus* |  |  | yes | yes |  |
| *Blastomyces dermatitidis* | yes | yes |  | yes |  |
| *Candida species* | yes | yes | yes | yes | yes |
| *Coccidioides immitis* | yes | yes |  | yes |  |
| *Cryptococcus neoformans* | yes | yes |  | yes |  |
| *Fusarium species* |  |  | yes |  |  |
| *Histoplasma capsulatum* | yes |  |  | yes |  |
| *Histoplasma duboisii* |  | yes |  |  |  |
| *Leishmania donovani* |  |  |  | yes |  |
| *Leishmania infantum* |  |  |  | yes |  |
| *Paracoccidioides brasiliensis* |  | yes |  | yes |  |
| *Scedosporium apiospermum* |  |  | yes |  |  |
| *Sporothrix schenckii* |  | yes |  |  |  |
| *Trichophyton mentagrophytes* |  | yes |  |  |  |
| *Trichophyton rubrum* |  | yes |  |  |  |

Preferred antibiotics include, but are not limited to, amikacin, amoxicillin, gentamicin, kanamycin, neomycin, netilmicin, paromomycin, tobramycin, geldanamycin, herbimycin, carbacephem (loracarbef), ertapenem, doripenem, imipenem, cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, ceftobiprole, clarithromycin, clavulanic acid, clindamycin, colistimethate teicoplanin, azithromycin, dirithromycin, erythromycin, troleandomycin, telithromycin, aztreonam, ampicillin, azlocillin, bacampicillin, carbenicillin, cloxacillin, dicloxacillin, flucloxacillin, mezlocillin, meticillin, nafcillin, norfloxacin, oxacillin, penicillin G, penicillin V, piperacillin, pvampicillin, pivmecillinam, ticarcillin, bacitracin, colistin, colimycin, polymyxin B, ciprofloxacin, enoxacin, gatifloxacin, levofloxacin, lomefloxacin, moxifloxacin, ofloxacin, trovafloxacin, grepafloxacin, sparfloxacin, afenide, prontosil, sulfacetamide, metronidazole, sulfamethizole, sulfanilimide, sulfamethoxazole, sulfisoxazole, trimethoprim, trimethoprim-sulfamethoxazole, demeclocycline, doxycycline, oxytetracycline, tetracycline, arsphenamine, chloramphenicol, chlorhexidine, lincomycin, ethambutol, fosfomycin, furazolidone, isoniazid, linezolid, mupirocin, nitrofurantoin, platensimycin, pyrazinamide, quinupristin/dalfopristin, rifampin, thiamphenicol, rifampicin, minocycline, sultamicillin, sulbactam, sulphonamides, mitomycin, spectinomycin, spiramycin, roxithromycin, and meropenem.

Other preferred antibiotics are described herein. Many of these, including azithromycin and sulfamethoxazole/trimethoprim are typically viewed as safe in a wide variety of patient populations and are dosed orally (and swallowed) in pediatric patients. Levofloxacin is a third generation quinolone that is typically reserved for those over 18 years of age or those considered "full grown." Ceftriaxone is a third generation cephalosporin that is already in powder form and is often dosed (intravenously) in pediatrics at 100 mg/kg/day (up to 4 grams/day) divided twice daily which would give a prescriber anticipated confidence in dosing the same orally as not being problematic. Meropenem is a carbapenem that is already in powder form and is often dosed (intravenously) in pediatrics at 40 mg/kg IV every 8 hours for ages 3 months or older which would give a prescriber anticipated confidence in dosing the same orally as not being problematic.

Expected coverage for various antibiotic agents is shown in Tables 2 and 3 below.

TABLE 2

|  | Gram | Bactroban | Ceftriaxone | Vancomycin | Colistimethate | Ciprofloxacin |
|---|---|---|---|---|---|---|
| *Bacteroides fragilis* | anaer |  | yes | no | no | no |
| *Clostridium difficile* | anaer |  | no | yes | no | no |
| *Clostridium perfringens* | anaer | no | yes | no |  |  |
| *Chlamydia pneumoniae* | n/a |  | no | no | no | yes |
| *Chlamydia psittaci* | n/a |  | no | no | no |  |
| *Chlamydia trachomatis* | n/a |  | no | no | no |  |
| *Mycoplasma pneumoniae* | n/a |  | no | no | no | yes |
| *Acinetobacter baumannii* | neg | no | no | no | ± | ± |
| *Acinetobacter calcoaceticus* | neg | no | no | no | ± | ± |
| *Acinetobacter lwoffii* | neg | no | no | no | ± | ± |
| *Bartonella bacilliformis* | neg | no | ± | no |  | yes |
| *Bordetella pertussis* | neg | no | no | no | no | ± |
| *Brucella species* | neg | no | ± | no | no | ± |
| *Campylobacter jejuni* | neg | no | no | no |  | yes |
| *Citrobacter diversus* | neg | no | yes | no |  | yes |
| *Citrobacter freundii* | neg | no | yes | no |  | yes |
| *Enterobacter aerogenes* | neg | no | yes | no | yes | yes |
| *Enterobacter cloacae* | neg | no | yes | no | yes | yes |
| *Enterobacter sakazakii* | neg | no | yes | no | yes |  |
| *Escherichia coli* | neg | no | yes | no | yes | yes |
| *Francisella tularensis* | neg | no | no | no |  | yes |
| *Haemophilus ducreyi* | neg | no | yes | no |  |  |
| *Haemophilus influenzae* | neg | no | yes | no |  | yes |
| *Haemophilus parainfluenzae* | neg |  | yes | no | no | yes |
| *Klebsiella (Calymmatobacterium) granulomatis* | neg | no | yes | no | yes |  |
| *Klebsiella oxytoca* | neg | no | yes | no | yes | yes |
| *Klebsiella pneumoniae* | neg | no | yes | no | yes | yes |
| *Legionella pneumophila* | neg | no | no | no | no | yes |

TABLE 2-continued

|  | Gram | Bactroban | Ceftriaxone | Vancomycin | Colistimethate | Ciprofloxacin |
|---|---|---|---|---|---|---|
| *Moraxella catarrhalis* | neg | no | yes | no | no | yes |
| *Morganella morganii* | neg | no | yes | no |  | yes |
| *Neisseria gonorrhoeae* | neg | no | yes | no | no | yes |
| *Neisseria meningitidis* | neg | no | yes | no | no | yes |
| *Proteus mirabilis* | neg | no | yes | no | no | yes |
| *Proteus vulgaris* | neg | no | yes | no | no | yes |
| *Providencia rettgeri* | neg | no | yes | no | no | yes |
| *Providencia stuartii* | neg | no | yes | no | no | yes |
| *Pseudomonas aeruginosa* | neg | no | no | no | yes | yes |
| *Pseudomonas fluorescens* | neg | no | ± | no | yes | yes |
| *Rickettsiae* | neg | no | no | no |  | yes |
| *Salmonella typhi* | neg | no | yes | no |  | yes |
| *Serratia marcescens* | neg | no | yes | no | no | yes |
| *Shigella boydii* | neg | no | yes | no |  | yes |
| *Shigella dysenteriae* | neg | no | yes | no |  | yes |
| *Shigella flexneri* | neg | no | yes | no |  | yes |
| *Shigella sonnei* | neg | no | yes | no |  | yes |
| *Vibrio cholerae* | neg | no | no | no | no | yes |
| *Yersinia pestis* | neg | no | no | no |  | yes |
| *Corynebacterium jeikeium* | pos | no | no | yes | no | no |
| *Corynebacterium urealyticum* | pos | no | no | yes | no | ± |
| *Diphtheroids* | pos |  | no | yes | no |  |
| *Enterococcus faecalis* | pos |  | no | yes | no | ± |
| *Enterococcus faecium* | pos |  | no | yes, not VRE | no | no |
| Methicillin Resistant *Staph aureus* (MRSA) | pos | yes | no | yes | no | no |
| *Peptostreptococcus* | pos |  | yes | yes | no | ± |
| *Staphylococcus aureus* (MSSA) | pos | yes | yes | yes | no | ± |
| *Staphylococcus epidermidis* | pos |  | yes | yes | no | yes |
| *Streptococcus agalactiae* | pos |  | yes | yes | no | ± |
| *Streptococcus pneumoniae* | pos |  | yes | yes | no | ± |
| *Streptococcus pyogenes* | pos | yes | yes | yes | no | ± |
| Viridans group streptococci | pos |  | yes | yes | no | ± |

TABLE 3

|  | Levo-floxacin | Tobramycin | Doxycycline | Azithromycin | Clindamycin | Sulfa/Trim |
|---|---|---|---|---|---|---|
| *Bacteroides fragilis* | no | no | ± | no | yes | no |
| *Clostridium difficile* | no | no | ± | no | ± | no |
| *Clostridium perfringens* | yes | no |  | no | yes - partial | no |
| *Chlamydia pneumoniae* | yes | no | yes | yes | ± | no |

TABLE 3-continued

| | Levo-floxacin | Tobramycin | Doxycycline | Azithromycin | Clindamycin | Sulfa/Trim |
|---|---|---|---|---|---|---|
| *Chlamydia psittaci* | | no | yes | yes | no | no |
| *Chlamydia trachomatis* | | no | yes | yes | no | no |
| *Mycoplasma pneumoniae* | yes | no | ± | yes | no | no |
| *Acinetobacter baumannii* | ± | no | no | no | no | ± |
| *Acinetobacter calcoaceticus* | ± | no | ± | no | no | ± |
| *Acinetobacter lwoffii* | ± | no | no | no | no | ± |
| *Bartonella bacilliformis* | yes | ± | yes | yes | no | yes |
| *Bordetella pertussis* | ± | no | | yes | no | yes |
| *Brucella species* | ± | ± | yes | no | no | yes |
| *Campylobacter jejuni* | yes | yes | yes | yes | no | no |
| *Citrobacter diversus* | yes | yes | no | no | no | no |
| *Citrobacter freundii* | yes | yes | no | no | no | no |
| *Enterobacter aerogenes* | yes | yes | ± | no | no | yes |
| *Enterobacter cloacae* | yes | yes | ± | no | no | yes |
| *Enterobacter sakazakii* | yes | yes | ± | no | no | no |
| *Escherichia coli* | yes | yes | ± | no | no | yes |
| *Francisella tularensis* | yes | ± | yes | no | no | no |
| *Haemophilus ducreyi* | | yes | yes | | | ± |
| *Haemophilus influenzae* | yes | yes | yes | yes | no | ± |
| *Haemophilus parainfluenzae* | yes | | yes | | no | no |
| *Klebsiella (Calymmatobacterium) granulomatis* | | yes | yes | no | no | yes |
| *Klebsiella oxytoca* | yes | yes | ± | no | no | yes |
| *Klebsiella pneumoniae* | yes | yes | ± | no | no | yes |
| *Legionella pneumophila* | yes | no | yes | yes | no | no |
| *Moraxella catarrhalis* | yes | yes | yes | yes | no | yes |
| *Morganella morganii* | yes | ± | no | no | no | yes |
| *Neisseria gonorrhoeae* | yes | no | ± | ± | no | ± |
| *Neisseria meningitidis* | yes | no | yes | yes | no | yes |
| *Proteus mirabilis* | yes | yes | no | no | no | no |
| *Proteus vulgaris* | yes | yes | no | no | no | no |
| *Providencia rettgeri* | yes | ± | no | no | no | ± |
| *Providencia stuartii* | yes | ± | no | no | no | ± |
| *Pseudomonas aeruginosa* | yes | yes | no | no | no | no |
| *Pseudomonas fluorescens* | yes | yes | | no | no | ± |
| *Rickettsiae* | yes | | yes | yes | no | no |
| *Salmonella typhi* | yes | | ± | ± | no | ± |
| *Serratia marcescens* | yes | yes | no | no | no | ± |
| *Shigella boydii* | yes | yes | ± | ± | no | ± |

TABLE 3-continued

| | Levo-floxacin | Tobramycin | Doxycycline | Azithromycin | Clindamycin | Sulfa/Trim |
|---|---|---|---|---|---|---|
| Shigella dysenteriae | yes | yes | ± | ± | no | ± |
| Shigella flexneri | yes | yes | ± | ± | no | ± |
| Shigella sonnei | yes | yes | ± | ± | no | ± |
| Vibrio cholerae | yes | no | yes | yes | no | yes |
| Yersinia pestis | yes | yes | yes | ± | no | yes |
| Corynebacterium jeikeium | no | no | | no | | |
| Corynebacterium urealyticum | ± | no | ± | ± | | no |
| Diphtheroids | | no | | | | |
| Enterococcus faecalis | yes | no | no | no | no | no |
| Enterococcus faecium | no | no | no | no | no | ± |
| Methicillin Resistant Staph aureus (MRSA) | no | no | ± | no | no | yes |
| Peptostreptococcus | ± | no | ± | ± | yes | yes |
| Staphylococcus aureus (MSSA) | yes | no | ± | yes | yes | yes |
| Staphylococcus epidermidis | yes | no | yes | yes | yes | yes |
| Streptococcus agalactiae | yes | no | ± | yes | yes | yes |
| Streptococcus pneumoniae | yes | no | yes | yes | yes | yes |
| Streptococcus pyogenes | yes | no | ± | yes | yes | ± |
| Viridans group streptococci | yes | no | ± | ± | yes | yes |

I. Formulations and Methods for Topical Oral Delivery

Preferred dry formulations for topical oral delivery include formulations containing the following combinations of ingredients:

1 to 100 mg azithromycin; 1 to 5 mg fluticasone, and 1 to 50 mg fluconazole.

1 to 100 mg sulfamethoxazole, 1 to 50 mg trimethoprim, 1 to 5 mg fluticasone, and 1 to 50 mg fluconazole.

1 to 150 mg levofloxacin hemihydrate, 1 to 5 mg fluticasone, and 1 to 50 mg fluconazole;

1 to 5 mg fluticasone, and 1 to 50 mg fluconazole; and 1 to 5 mg fluticasone.

Any of the above formulations can be dispensed with any of the following a composition comprising 1 to 1500 mg ceftriaxone, 1 to 5 mg betamethasone, and 1 to 50 mg fluconazole;

a composition comprising 1 to 1500 mg meropenem, 1 to 5 mg betamethasone, and 1 to 50 mg fluconazole.

a composition comprising 1 to 50 mg lidocaine hydrochloride, preferably 20 mg.

a composition comprising 1 to 200 mg acyclovir.

Acyclovir is an antiviral medication that is not often utilized in the pediatric arena although it can be dosed down to three months of age in a depressed dosing regimen. It can be used in older patients dealing with viral issues in the oral cavity. Lidocaine is a local anesthetic and can be used to help treat pain in the oral cavity. It is typically utilized in a swish/spit methodology although swish/swallow is sometimes utilized.

Preferred dry formulations for topical oral administration include amounts given above in the following ratios:

5% azithromycin, 1.5% fluticasone, and 1.5% fluconazole.

8% sulfamethoxazole, 5% trimethoprim, 1.5% fluticasone, and 1.5% fluconazole.

12.8% levofloxacin hemihydrate, 1.5% fluticasone, and 1.5% fluconazole.

1.5% fluticasone and 1.5% fluconazole.

1.5% fluticasone.

Any of the above formulations can be dispensed with any of the following:

a) ceftriaxone, betamethasone, and fluconazole. Preferred amounts are 500 mg ceftriaxone, 0.75 mg betamethasone, and 0.75 mg fluconazole.

b) meropenem, betamethasone, and fluconazole. Preferred amounts are 500 mg meropenem, 0.75 mg betamethasone, and 0.75 mg fluconazole.

c) lidocaine. A preferred amount is 20 mg lidocaine hydrochloride.

d) acyclovir. A preferred amount is 200 mg acyclovir.

In preferred embodiments, the dry formulation for topical oral administration does not contain an antihistamine.

In some embodiments, the formulations of the invention comprise the listed active ingredients. In other embodiments the formulations of the invention consist of the listed ingredients and a pharmaceutically acceptable carrier. The phrase "consisting essentially of" limits a composition to the specified materials or steps and those additional, undefined components that do not materially affect the basic and novel characteristic(s) of the composition, such as, for example, additional active ingredients. In still other embodiments, the formulations of the invention consist of the listed active ingredients and a pharmaceutically acceptable carrier. "Consisting of" refers to the inclusion of exactly one element of a number or list of elements.

Also included is a method of preparing an orally administrable formulation comprising forming a dry formulation for oral administration into an oral rinse or an oral solution. For example, the compositions described herein may be incorporated into mouthwash formulations for oral administration as an oral rinse. The dry formulation compositions may be combined with any known mouthwash base material.

The oral rinse or solution base material may comprise a diphenhydramine elixir such as Benadryl®, or a generic equivalent. In some embodiments, the concentration of diphenhydramine in the elixir is 12.5 mg/5 mL. The base material may also comprise aluminium hydroxide and/or magnesium hydroxide, including Maalox® (MgOH & AlOH; 40 mg/ml), or a generic equivalent, Mylanta, or a generic equivalent. Other agents that can be included in the base material include a local anesthetic such as lidocaine or Dyclone, nystatin, sucralfate, Kaopectate, allopurinol, vitamin E, beta-carotene, Kamillosan liquid, aspirin, antiprostaglandins, prostaglandins, MGI 209 (marketed as Oratect Gel), silver nitrate, and antiviral agents such as acyclovir. Other suitable oral rinse base material may include Prevident® or Phos-Flur® rinses.

In the case of an oral rinse, the patient is instructed to mix the contents of 1 capsule or vial with about 10 mL of the desired base material. The preparation is to be swished around in the mouth for an appropriate length of time, e.g., at least about 1-3 minutes, then expectorated. This is also known a swish/spit methodology.

In the case of an oral solution, the patient is instructed to mix the contents of 1 capsule or vial with about 10 mL of the desired base material. The preparation is to be swished around in the mouth for an appropriate length of time, e.g., at least about 1-3 minutes, then swallowed. Typically, the administration is three times daily. This is also known a swish/swallow methodology.

The oral rinses and solutions described are useful for treating a variety of disorders affecting the mucosal surfaces of the upper alimentary canal, including the oral mucosa, lips, and perioral region of the face of a mammal, preferably a human. The oral mucosa is the mucous membrane epithelium of the mouth. It can be divided into three categories— the masticatory mucosa, the lining mucosa, and the specialized mucosa. The lips surround the mouth and the entrance of the oral cavity, and the perioral region includes the skin surrounding the lips and mouth.

Medical conditions in this area can be problematical, inconvenient to treat, and painful to endure. Furthermore, the impact of oral diseases does not stop at the mouth and teeth. A growing body of evidence has linked oral health, particularly periodontal (gum) disease, to several chronic diseases including diabetes, heart disease, and stroke.

Dental caries is most common chronic disease in the world. Tooth decay affects more than 1 out of 4 US children ages 2 to 5, 1 out of 2 in US children ages 12 to 15. Oral diseases cause pain and disability for millions of Americans. Gum disease and other oral issues typically caused by presence of acid-producing bacteria in the mouth and typically worsens as age increases. These conditions and others are contemplated for treatment with the formulations of the present invention.

For example, cheilitis involves the inflammation of the lip. The types of cheilitis are exfoliative, allergic, actinic, glandular, bacterial, and others. Other common superficial lesions of the oral mucosa, lips, and perioral region include candidiasis, recurrent herpes labialis, recurrent aphthous stomatitis, erythema migrans, hairy tongue, lichen planus, eosinophilic esophagitis, and ulcer.

The condition treated may be caused by or the result of an antineoplastic therapy, such as chemotherapy or radiation therapy. The condition may also be caused by or the result of gingivitis. The condition may also be caused by or the result of a bacterial, viral or fungal infection.

II. Formulations and Methods for Topical Nasal/Upper Respiratory Delivery

Dry formulations for nasal or upper respiratory delivery include formulations containing the following combinations of ingredients:

1 to 150 mg levofloxacin, 1 to 200 mg mupirocin, 1 to 5 mg fluticasone, and 1 to 100 mg itraconazole.

1 to 150 mg levofloxacin, 1 to 5 mg fluticasone, and 1 to 100 mg itraconazole.

1 to 150 mg levofloxacin, 1 to 5 mg fluticasone, and 1 to 15 mg amphotericin B.

1 to 150 mg tobramycin, 1 to 5 mg fluticasone, and 1 to 100 mg itraconazole.

1 to 150 mg tobramycin, 1 to 5 mg fluticasone, and 1 to 15 mg amphotericin B.

1 to 200 mg mupirocin, 1 to 5 mg fluticasone, and 1 to 100 mg itraconazole.

1 to 200 mg mupirocin, 1 to 5 mg fluticasone, and 1 to 15 mg amphotericin B.

1 to 100 mg vancomycin hydrochloride, 1 to 5 mg fluticasone, and 1 to 100 mg itraconazole.

1 to 100 mg vancomycin hydrochloride, 1 to 5 mg fluticasone, and 1 to 15 mg amphotericin B.

1 to 50 mg tobramycin, 1 to 200 mg mupirocin.

1 to 5 mg fluticasone and 1 to 15 mg amphotericin B.

1 to 5 mg fluticasone and 1 to 100 mg itraconazole.

In some embodiments of these dry formulations, the pharmaceutically acceptable excipients or additives include a base for use in pharmaceutical compounding and manufacturing of topical preparations.

Preferred dry formulations for nasal or upper respiratory delivery include:

levofloxacin hemihydrate, 10% mupirocin, 1.5% fluticasone, and 5% itraconazole.

12.8% levofloxacin hemihydrate, 1.5% fluticasone, and 5% itraconazole.

12.8% levofloxacin hemihydrate, 1.5% fluticasone, and 1% amphotericin B.

16% tobramycin, 1.5% fluticasone, and 5% itraconazole.

16% tobramycin, 1.5% fluticasone, and 1% amphotericin B.

10% mupirocin, 1.5% fluticasone, and 5% itraconazole.

10% mupirocin, 1.5% fluticasone, and 1% amphotericin B.

5.15% vancomycin hydrochloride, 1.5% fluticasone, and 5% itraconazole.

5.15% vancomycin hydrochloride, 1.5% fluticasone, and 1% amphotericin B.

16% tobramycin, 20% mupirocin.

1.5% fluticasone and 1% amphotericin B.

1.5% fluticasone and 5% itraconazole.

The disclosure also provides a dry formulation or nasal or upper respiratory delivery comprising one or more of the following actives in combination with pharmaceutically acceptable excipients or additives: a) at least one leukotriene receptor antagonist; b) at least one anti-inflammatory steroid; and c) at least one non-sedative antihistamine.

In one embodiment, the formulation comprises the following actives: 1 to 5 mg montelukast, 1 to 5 mg fluticasone, and 1 to 5 mg levocetirizine.

In other embodiments, the formulation comprises the following actives: 0.3% montelukast, 1.5% fluticasone, 0.2% levocetirizine dihydrochloride.

Also included is a method for preparing an intranasally administrable formulation comprising forming a dry formulation into a nasal solution or suspension with a diluent suitable for intranasal delivery of active ingredients. For example, a liquid spray or a nebulized powder allowing the active ingredient to be delivered into the nasal or nasopharyngeal cavity is contemplated. It is noted that the dry formulations described herein are not intended for administration as powders.

Diluents for the preparation of intranasally administrable formulations are known to those skilled in the art, for example 0.9% sodium chloride, which is available in vials and with a prescription or over the counter.

In some embodiments, the formed composition is administrable by a nasal nebulizer. Suitable devices include the NASONEB® system and the SINUSTAR® system. Other suitable devices include Micromist (Hudson RCl), Pulmo-Aide (Devilbiss), Sidestream, MS 2400 (Invacare), and Pari LC Star (Pari Respiratory equipment).

In other embodiments, the typical mode of administration is in flush form or liquid stream form. An example of suitable sinus rinse delivery mechanisms include the NeilMed® Sinus Rinse Bottle, a medical syringe of about 20 to 60 ml in size, and other squeeze bottle irrigation devices.

Typically, the intranasally administrable formulation is administered two or three times a day.

Also included is a method for treating inflammatory, ulcerative and painful conditions of the respiratory tract, respiratory airways or lungs of a mammal comprising administering an intranasally administrable formulation as described herein. The administering can be any suitable means, including inhalation, spraying, liquid stream lavage, nebulizing, or nasal irrigation. Further, administration can be directed to the sinus cavity or the lungs, for instance.

The inflammatory, ulcerative and painful condition of the respiratory tract, respiratory airways or lungs can include a condition caused by a bacterial, viral, or fungal infection, including a pseudomonas infection or a MRSA infection, influenza and the common cold. Other conditions contemplated include an upper respiratory tract infection lower respiratory tract infection, cystic fibrosis, bronchiolitis, bronchiectasis, tracheobronchitis, pneumonia (including ventilator-associated pneumonia, pneumonitis, dyspnea, cough, (recurrent) wheezing, asthma, nasal polyopsis, allergic rhinitis, upper respiratory infections (Common cold), pulmonary sarcoidosis, anosmia, olfactory (smell) loss, sinus ostia stenosis, aspergilliosis, pulmonary invasive fungal infections, sinusitis, chronic rhinosinusitis, nosocomial lung infections.

III. Formulations and Methods for Aural Delivery

Dry formulations for aural delivery include formulations containing the following combinations of ingredients:

1 mg to 50 mg azithromycin, 1 mg to 5 mg fluticasone, and 1 mg to 50 mg fluconazole.

1 mg to 180 mg sulfamethoxazole, 1 mg to 50 mg trimethoprim, 1 mg to 5 mg fluticasone, and 1 mg to 50 mg fluconazole.

1 mg to 150 mg levofloxacin hemihydrate, 1 mg to 5 mg fluticasone, and 1 mg to 50 mg fluconazole.

1 mg to 5 mg fluticasone and 1 mg to 50 mg fluconazole.

1 to 100 mg vancomycin hydrochloride and 1 to 200 mg mupirocin.

Preferred Dry Formulations for Aural Delivery Include:

5% azithromycin, 1.5% fluticasone, and 1.5% fluconazole.

8% sulfamethoxazole, 5% trimethoprim, 1.5% fluticasone, and 1.5% fluconazole.

12.8% levofloxacin hemihydrate, 1.5% fluticasone, and 1.5% fluconazole.

1.5% fluticasone and 1.5% fluconazole.

5.15% vancomycin hydrochloride, 20% mupirocin,

Any of the above formulations can be dispensed with any of the following:

a) ceftriaxone, betamethasone, and fluconazole. Preferred amounts are 500 mg ceftriaxone, 0.75 mg betamethasone, and 0.75 mg fluconazole.

Also included is a method of preparing a formulation for aural administration comprising forming a dry formulation as described herein into a solution or suspension with a diluent suitable for otic delivery of active ingredient. Diluents for the preparation of formulations for aural administration are known to those skilled in the art and are similar to those described above for the preparation of intranasally administrable formulations.

The resulting solution or suspension can be administered to the ear or ear canal. For example, the solution or suspension can be drawn into a syringe and then dispensed into the ear canal. For such administration, the solution should not be cold. For instance, the solution can be warmed by holding the container in the hand for one or two minutes to avoid dizziness which may result from the instillation of a cold solution. The patient should lie with the affected ear upward, and then the medication should be instilled. The ear canal should be completely filled to ensure that medication is allowed to touch all areas of the ear canal. The process can be repeated for other ear if needed.

Also included is a method for treating inflammatory, ulcerative and painful conditions of the ear of a mammal comprising administering to said mammal a formulation for aural administration as described herein. As noted the administering may be by instillation of the solution or suspension into the ear canal. In general, the administering is two to three times daily.

The inflammatory, ulcerative and painful conditions of the ear can include, for example, otitis externa, otitis media, otorrhea, acute mastoiditis, otosclerosis, otic pain, otic bleeding, otic inflammation, Lermoyez's syndrome, Meniere's disease, vestibular neuronitis, benign paroxysmal positional vertigo, herpes zoster oticus, Ramsay Hunt's syndrome, viral neuronitis, ganglionitis, geniculate herpes, labyrinthitis, purulent labyrinthitis, perilymph fistulas, presbycusis, drug-induced ototoxicity, acoustic neuromas, aerotitis media, infectious myringitis, bullous myringitis, squamous cell carcinoma, basal cell carcinoma, pre-cancerous otic conditions, nonchromaffin paragangliomas, chemodectomas, glomus jugulare tumors, glomus tympanicum tumors, perichondritis, aural eczematoid dermatitis, malignant external otitis, subperichondrial hematoma, ceruminomas, impacted cerumen, sebaceous cysts, osteomas, keloids, otalgia, tinnitus, vertigo, tympanic membrane infection, tympanitis, otic furuncles, petrositis, conductive and sensorineural hearing loss, epidural abscess, lateral sinus thrombosis, subdural empyema, otitic hydrocephalus, Dandy's syndrome, bullous myringitis, diffuse external otitis, foreign bodies, keratosis obturans, otic neoplasm, otomycosis, trauma, acute barotitis media, acute eustachian tube obstruction, postsurgical otalgia, cholesteatoma, and infections related to an otic surgical procedure.

IV. Representative Method of Compounding

A method of compounding may include combining the active ingredients with a base composition and shaking or otherwise mixing the combined ingredients, sifting the resulting powder mixture through a fine mesh strainer, mixing the powdered mixture until a homogeneous powder results. A suitable mixer for this purpose is a TURBULA® mixer, which is able to mix powdery substances with differing specific weights and particle sizes. The mixing is generally performed for about one hour. The resulting homogeneous mixture can be encapsulated into a suitable capsule, for example a #00 size capsule.

VI. Exemplary Storage Characteristics

The dry formulations discussed herein exhibit excellent storage characteristics. The dry formulations described herein are stable for at least about 6 months, or about 180 days.

Certain preferred features are provided by the following numbered clauses:

Clause 1. A dry formulation comprising one or more of the following actives in combination with pharmaceutically acceptable excipients or additives:
 a) at least one antibiotic;
 b) at least one anti-inflammatory steroid; and
 c) at least one antifungal agent.

Clause 2. The dry formulation of clause 1, wherein all of actives (a) to (c) are included.

Clause 3. The dry formulation of clause 1, wherein the dry formulation is formulated as a capsule.

Clause 4. The dry formulation of clause 1, wherein the pharmaceutically acceptable excipients or additives comprise: at least one solvent, at least one emollient, at least one humectant, at least one preservative, and at least one emulsifier; and optionally including an acid, base, or buffering agent to adjust the pH.

Clause 5. The dry formulation of clause 1, wherein the pharmaceutically acceptable excipients or additives include a base for use in pharmaceutical compounding and manufacturing of topical preparations.

Clause 6. The dry formulation of clause 1, wherein the dry formulation does not contain an antihistamine.

Clause 7. The dry formulation of clause 1, wherein the dry formulation is stable for 180 days.

Clause 8. The dry formulation of clause 1 comprising the following actives: 5% azithromycin, 1.5% fluticasone, and 1.5% fluconazole.

Clause 9. The dry formulation of clause 1 comprising the following actives: 8% sulfamethoxazole, 5% trimethoprim, 1.5% fluticasone, and 1.5% fluconazole.

Clause 10. The dry formulation of clause 1 comprising the following actives: 12.8% levofloxacin hemihydrate, 1.5% fluticasone, and 1.5% fluconazole.

Clause 11. The dry formulation of clause 1 comprising the following actives: 1.5% fluticasone and 1.5% fluconazole.

Clause 12. The dry formulation of clause 1 comprising the following actives: 1.5% fluticasone, wherein the pharmaceutically acceptable excipients or additives include a base for use in pharmaceutical compounding and manufacturing of topical preparations.

Clause 13. A method of preparing an orally administrable formulation comprising forming the dry formulation of clause 1 into an oral rinse or an oral solution.

Clause 14. The method of clause 13, wherein the oral rinse comprises diphenhydramine.

Clause 15. The method of clause 13, wherein the oral solution comprises aluminium hydroxide, magnesium hydroxide and simethicone.

Clause 16. The method of clause 13, further comprising forming a local anesthetic into the oral rinse or oral solution.

Clause 17. The method of clause 16, wherein the local anesthetic is lidocaine.

Clause 18. The method of clause 13, further comprising forming an antiviral agent into the oral rinse or oral solution.

Clause 19. The method of clause 18, wherein the antiviral agent is acyclovir.

Clause 20. An orally administrable formulation obtained by the method of clause 13.

Clause 21. A method for treating inflammatory, ulcerative and painful conditions of mucosal surfaces of the upper alimentary canal of a mammal comprising administering to said patient the orally administrable formulation of clause 20.

Clause 22. The method of clause 21, wherein the orally administrable formulation is an oral rinse and wherein the method comprises:
 (1) swishing the oral rinse formulation; and
 (2) expectorating the oral rinse formulation.

Clause 23. The method of clause 21, wherein the orally administrable formulation is an oral solution and wherein the method comprises:
 (1) swishing the oral solution; and
 (2) swallowing the oral solution.

Clause 24. The method of clause 21, wherein said mammal is a human.

Clause 25. The method of clause 21, wherein the condition is mucositis.

Clause 26. The method of clause 21, wherein the condition is aphthous stomatitis.

Clause 27. The method of clause 21, wherein the condition is oral lichen planus.

Clause 28. The method of clause 21, wherein the condition is eosinophilic esophogitis Clause 29. The method of clause 21, wherein the condition is an ulcer.

Clause 30. The method of clause 21, wherein the condition is caused by antineoplastic therapy.

Clause 31. The method of clause 30, wherein said antineoplastic therapy is radiation therapy.

Clause 32. The method of clause 30, wherein said antineoplastic therapy is chemotherapy.

Clause 33. The method of clause 21, wherein the condition is the result of gingivitis.

Clause 34. The method of clause 21, wherein the condition is the result of tooth extraction.

Clause 35. The method of clause 21, wherein the condition is caused by a bacterial, viral, or fungal infection.

Clause 36. The method of clause 35, wherein the infection is selected from the group consisting of candidias and herpes labialis Clause 37. The method of clause 35, wherein the condition is erythema migrans.

Clause 38. The dry formulation of clause 1 comprising the following actives: 12.8% levofloxacin hemihydrate, 10% mupirocin, 1.5% fluticasone, and 5% itraconazole.

Clause 39. The dry formulation of clause 1 comprising the following actives: 12.8% levofloxacin hemihydrate, 1.5% fluticasone, and 5% itraconazole.

Clause 40. The dry formulation of clause 1 comprising the following actives: 12.8% levofloxacin hemihydrate, 1.5% fluticasone, and 1% amphotericin B.

Clause 41. The dry formulation of clause 1 comprising the following actives: 16% tobramycin, 1.5% fluticasone, and 5% itraconazole.

Clause 42. The dry formulation of clause 1 comprising the following actives: 16% tobramycin, 1.5% fluticasone, and 1% amphotericin B.

Clause 43. The dry formulation of clause 1 comprising the following actives: 10% mupirocin, 1.5% fluticasone, and 5% itraconazole.

Clause 44. The dry formulation of clause 1 comprising the following actives: 10% mupirocin, 1.5% fluticasone, and 1% amphotericin B.

Clause 45. The dry formulation of clause 1 comprising the following actives: 5.15% vancomycin hydrochloride, 1.5% fluticasone, and 5% itraconazole.

Clause 46. The dry formulation of clause 1 comprising the following actives: 5.15% vancomycin hydrochloride, 1.5% fluticasone, and 1% amphotericin B.

Clause 47. The dry formulation of clause 1, comprising the following actives: 16% tobramycin, 20% mupirocin, wherein the pharmaceutically acceptable excipients or additives include a base for use in pharmaceutical compounding and manufacturing of topical preparations.

Clause 48. The dry formulation of clause 1 comprising the following actives: 1.5% fluticasone and 1% amphotericin B, wherein the pharmaceutically acceptable excipients or additives include a base for use in pharmaceutical compounding and manufacturing of topical preparations.

Clause 49. The dry formulation of clause 1 comprising the following actives: 1.5% fluticasone and 5% itraconazole, wherein the pharmaceutically acceptable excipients or additives include a base for use in pharmaceutical compounding and manufacturing of topical preparations.

Clause 50. A method of preparing an intranasally administrable formulation comprising forming the dry formulation of clause 1 into a nasal solution or suspension with a diluent suitable for intranasal delivery of active ingredients.

Clause 51. An intranasally administrable formulation obtained by the method of clause 50.

Clause 52. A method for treating inflammatory, ulcerative and painful conditions of the respiratory tract, respiratory airways or lungs of a mammal comprising administering to said mammal the intranasally administrable formulation of clause 51.

Clause 53. The method of clause 51, wherein the intranasally administrable formulation is administered by a method selected from the group consisting of inhalation, spraying, liquid stream lavage, nebulizing, and nasal irrigation.

Clause 54. The method of clause 53, wherein the administering is to the sinus cavity.

Clause 55. The method of clause 53, wherein the administering is to the lungs.

Clause 56. The method of clause 53, wherein the administering two or three times a day.

Clause 57. The method of clause 53, wherein the method is nebulizing.

Clause 58. The method of clause 53, wherein the method is nasal irrigation.

Clause 59. The method of clause 52, wherein said mammal is a human.

Clause 60. The method of clause 52, wherein the condition is caused by a bacterial, viral, or fungal infection.

Clause 61. The method of clause 60, wherein the infection is a pseudomonas infection.

Clause 62. The method of clause 60, wherein the infection is a MRSA infection.

Clause 63. The method of clause 52, wherein the condition is selected from the group consisting of an upper respiratory tract infection lower respiratory tract infection, bronchiolitis, pneumonia, dyspnea, cough, (recurrent) wheezing and asthma.

Clause 64. A dry formulation comprising one or more of the following actives in combination with pharmaceutically acceptable excipients or additives:
 a) at least one leukotriene receptor antagonist;
 b) at least one anti-inflammatory steroid; and
 c) at least one non-sedative antihistamine.

Clause 65. The dry formulation of clause 64 comprising the following actives: 0.3% montelukast, 1.5% fluticasone, 0.2% levocetirizine dihydrochloride.

Clause 66. The dry formulation of clause 64, comprising the following actives: 5.15% vancomycin hydrochloride, 20% mupirocin, wherein the pharmaceutically acceptable excipients or additives include a base for use in pharmaceutical compounding and manufacturing of topical preparations.

Clause 67. A method of preparing a formulation for aural administration comprising forming the dry formulation of clause 64 into a solution or suspension with a diluent suitable for otic delivery of active ingredients.

Clause 68. A formulation for aural administration obtained by the method of clause 67.

Clause 69. A method for treating inflammatory, ulcerative and painful conditions of the ear of a mammal comprising administering to said mammal the formulation for aural administration of clause 68.

Clause 70. The method of clause 68, wherein the formulation for aural administration is administered by instillation of the solution or suspension into the ear canal.

Clause 71. The method of clause 68, wherein the administering three times a day.

Clause 72. The method of clause 68, wherein the condition is selected from the group consisting of otitis externa, otitis media, otorrhea, acute mastoiditis, otosclerosis, otic pain, otic bleeding, otic inflammation, Lermoyez's syndrome, Meniere's disease, vestibular neuronitis, benign paroxysmal positional vertigo, herpes zoster oticus, Ramsay Hunt's syndrome, viral neuronitis, ganglionitis, geniculate herpes, labyrinthitis, purulent labyrinthitis, perilymph fistulas, presbycusis, drug-induced ototoxicity, acoustic neuromas, aerotitis media, infectious myringitis, bullous myringitis, squamous cell carcinoma, basal cell carcinoma, precancerous otic conditions, nonchromaffin paragangliomas, chemodectomas, glomus jugulare tumors, glomus tympanicum tumors, perichondritis, aural eczematoid dermatitis, malignant external otitis, subperichondrial hematoma, ceruminomas, impacted cerumen, sebaceous cysts, osteomas, keloids, otalgia, tinnitus, vertigo, tympanic membrane infection, tympanitis, otic furuncles, petrositis, conductive and sensorineural hearing loss, epidural abscess, lateral sinus thrombosis, subdural empyema, otitic hydrocephalus, Dandy's syndrome, bullous myringitis, diffuse external otitis, foreign bodies, keratosis obturans, otic neoplasm, otomycosis, trauma, acute barotitis media, acute eustachian tube obstruction, postsurgical otalgia, cholesteatoma, infections related to an otic surgical procedure.

The present invention may be embodied in other forms without departing from the spirit or essential attributes thereof and, accordingly, reference should be had to the following claims rather than the foregoing specification as indicating the scope of the invention. Further, the illustrations of arrangements described herein are intended to provide a general understanding of the various embodiments, and they are not intended to serve as a complete description. Many other arrangements will be apparent to those of skill in the art upon reviewing the above description. Other arrangements may be utilized and derived therefrom, such that logical substitutions and changes may be made without departing from the scope of this disclosure.

This disclosure is intended to cover any and all adaptations or variations of various embodiments and arrangements of the invention. Combinations of the above arrangements, and other arrangements not specifically described herein, will be apparent to those of skill in the art upon reviewing the above description. Therefore, it is intended that the disclosure not be limited to the particular arrangement(s) disclosed as the best mode contemplated for carrying out this invention, but that the invention will include all embodiments and arrangements falling within the scope of the appended claims.

The Abstract of the Disclosure is submitted with the understanding that it will not be used to interpret or limit the scope or meaning of the claims.

EXAMPLES

Example 1

Preparation of a Dry Formulation of 5% Azithromycin, 1.5% Fluticasone, and 1.5% Fluconazole 5 g azithromycin dihydrate powder, 1.5 g fluticasone 20% aliquot and 1.5 g fluconazole are combined with 61.7 g PCCA LOXASPERSE base and shaken well. The mixture is sifted through a fine mesh strainer. The mixture is then placed in a TURBULA® mixer and mixed for one hour. The resulting homogeneous powder is encapsulated into a capsule sized #00. Each capsule contains approximately 0.05 g azithromycin, 0.015 g fluticasone, 0.015 g fluconazole and 0.617 g LOXASPERSE.

Example 2

Preparation of a Dry Formulation of 8% Sulfamethoxazole, 5% Trimethoprim, 1.5% Fluticasone, And 1.5% Fluconazole 8 g sulfamethoxazole, 5 g micronized trimethoprim, 1.5 g fluticasone 20% aliquot and 1.5 g fluconazole are combined with 48.2 g PCCA LOXASPERSE base and mixed and encapsulated according to the procedure of Example 1. Each capsule contains approximately 0.08 g sulfamethoxazole, 0.05 g trimethoprim, 0.015 g fluticasone, 0.015 g fluconazole and 0.482 g LOXASPERSE.

Example 3

Preparation of a Dry Formulation of 12.8% Levofloxacin Hemihydrate, 1.5% Fluticasone, and 1.5% Fluconazole 12.8 g levofloxacin hemihydrate, 1.5 g fluticasone 20% aliquot and 1.5 g fluconazole are combined with 46.5 g PCCA LOXASPERSE base and mixed and encapsulated according to the procedure of Example 1. Each capsule contains approximately 0.128 g levofloxacin hemihydrate, 0.015 g fluticasone, 0.015 g fluconazole and 0.465 g LOXASPERSE. 5.12 mg levofloxacin hemihydrate equals 5 mg levofloxacin.

Example 4

Preparation of a Dry Formulation of 1.5% Fluticasone and 1.5% Fluconazole 1.5 g fluticasone 20% aliquot and 1.5 g fluconazole are combined with 67.7 g PCCA LOXASPERSE base and mixed and encapsulated according to the procedure of Example 1. Each capsule contains approximately 0.015 g fluticasone, 0.015 g fluconazole and 0.677 g LOXASPERSE.

Example 5

Preparation of a Dry Formulation of 1.5% Fluticasone 1.5 g fluticasone 20% aliquot is combined with 69.2 g PCCA LOXASPERSE base and mixed and encapsulated according to the procedure of Example 1. Each capsule contains approximately 0.015 g fluticasone and 0.692 g LOXASPERSE.

Example 6

Preparation of a Dry Formulation of 12.8% Levofloxacin Hemihydrate, 10% Mupirocin, 1.5% Fluticasone, and 5% Itraconazole 12.8 g levofloxacin hemihydrate, 10 g mupirocin, 1.5 g fluticasone 20% aliquot and 5 g micronized itraconazole are combined with 14.3 g PCCA LOXASPERSE base and mixed and encapsulated according to the procedure of Example 1. Each capsule contains approximately 0.128 g levofloxacin hemihydrate, 0.1 g mupirocin, 0.015 g fluticasone, 0.05 g itraconazole and 0.143 g LOXASPERSE.

Example 7

Preparation of a Dry Formulation of 12.8% Levofloxacin Hemihydrate, 1.5% Fluticasone, and 5% Itraconazole 12.8 g levofloxacin hemihydrate, 1.5 g fluticasone 20% aliquot and 5 g micronized itraconazole are combined with 43.7 g PCCA LOXASPERSE base and mixed and encapsulated according to the procedure of Example 1. Each capsule contains approximately 0.128 g levofloxacin hemihydrate, 0.015 g fluticasone, 0.05 g itraconazole and 0.437 g LOXASPERSE.

Example 8

Preparation of a Dry Formulation of 12.8% Levofloxacin Hemihydrate, 1.5% Fluticasone, and 1% Amphotericin B 12.8 g levofloxacin hemihydrate, 1.5 g fluticasone 20% aliquot and 1 g amphotericin B (oral grade) are combined with 47 g PCCA LOXASPERSE base and mixed and encapsulated according to the procedure of Example 1. Each capsule contains approximately 0.128 g levofloxacin hemihydrate, 0.015 g fluticasone, 0.01 g amphotercin B and 0.470 g LOXASPERSE.

Example 9

Preparation of a Dry Formulation of 16% Tobramycin, 1.5% Fluticasone, and 5% Itraconazole 16 g tobramycin, 1.5 g fluticasone 20% aliquot, 5 g micronized itraconazole and 6.18 g citric acid monohydrate are combined with 31.3 g PCCA LOXASPERSE base and mixed and encapsulated according to the procedure of Example 1. The citric acid is ground prior to mixing with the rest of the ingredients. Each capsule contains approximately 0.16 g tobramycin, 0.015 g fluticasone, 0.05 g itraconazole 0.0618 g citric acid and 0.313 g LOXASPERSE.

Example 10

Preparation of a Dry Formulation of 16% tobramycin, 1.5% Fluticasone, and 1% Amphotericin B 16 g tobramycin, 1.5 g fluticasone 20% aliquot, 1 g amphotericin B (oral grade) and 6.18 g citric acid monohydrate are combined with 34.6 g PCCA LOXASPERSE base and mixed and encapsulated according to the procedure of Example 1. The citric acid is ground prior to mixing with the rest of the ingredients. Each capsule contains approximately 0.16 g tobramycin, 0.015 g fluticasone, 0.01 g amphotercin B, 0.0618 g citric acid and 0.346 g LOXASPERSE.

Example 11

Preparation of a Dry Formulation of 10% Mupirocin, 1.5% Fluticasone, and 5% Itraconazole 10 g mupirocin, 1.5 g fluticasone 20% aliquot and 5 g micronized itraconazole are combined with 43 g PCCA LOXASPERSE base and mixed and encapsulated according to the procedure of Example 1. Each capsule contains approximately 0.1 g mupirocin, 0.015 g fluticasone, 0.05 g itraconazole and 0.43 g LOXASPERSE.

Example 12

Preparation of a Dry Formulation of 10% Mupirocin, 1.5% Fluticasone, and 1% Amphotericin B 10 g mupirocin, 1.5 g fluticasone 20% aliquot and 1 g amphotericin B (oral grade) are combined with 37.9 g PCCA LOXASPERSE base and mixed and encapsulated according to the procedure of Example 1. Each capsule contains approximately 0.1 g mupirocin, 0.015 g fluticasone, 0.01 amphotericin B and 0.379 g LOXASPERSE.

Example 13

Preparation of a Dry Formulation of 5.15% Vancomycin Hydrochloride, 1.5% Fluticasone, and 5% Itraconazole 5.15 g vancomycin hydrochloride, 1.5 g fluticasone 20% aliquot and 5 g micronized itraconazole are combined with 59 g PCCA LOXASPERSE base and mixed and encapsulated according to the procedure of Example 1. 1.03 g vancomycin hydrochloride equals 1 g vancomycin. Each capsule contains approximately 0.0515 g vancomycin hydrochloride, 0.015 g fluticasone, 0.05 g itraconazole and 0.59 g LOXASPERSE.

Example 14

Preparation of a Dry Formulation of 5.15% Vancomycin Hydrochloride, 1.5% Fluticasone, and 1% Amphotericin B 5.15 g vancomycin hydrochloride, 1.5 g fluticasone 20% aliquot and 1 g amphotericin B (oral grade) are combined with 62.3 g PCCA LOXASPERSE base and mixed and encapsulated according to the procedure of Example 1. Each capsule contains approximately 0.0515 g vancomycin hydrochloride, 0.015 g fluticasone, 0.01 amphotericin B and 0.623 g LOXASPERSE.

Example 15

Preparation of a Dry Formulation of 16% Tobramycin and 20% Mupirocin 16 g tobramycin, 20 g mupirocin and 6.18 g citric acid monohydrate are combined, mixed and encapsulated according to the procedure of Example 1. The citric acid is ground prior to mixing with the rest of the ingredients. Each capsule contains approximately 0.16 g tobramycin, 0.2 g mupirocin, and 0.0618 g citric acid.

Example 16

Preparation of a Dry Formulation of 1.5% Fluticasone and 1% Amphotericin B 1.5 g fluticasone 20% aliquot and 1 g amphotericin B (oral grade) are combined with 67.2 g PCCA LOXASPERSE base and mixed and encapsulated according to the procedure of Example 1. Each capsule contains approximately 0.015 g fluticasone, 0.01 g amphotericin B and 0.672 g LOXASPERSE.

Example 17

Preparation of a Dry Formulation of 1.5% Fluticasone and 5% Itraconazole, Wherein the Pharmaceutically Acceptable Excipients or Additives Include a Base for Use in Pharmaceutical Compounding and Manufacturing of Topical Preparations 1.5 g fluticasone 20% aliquot and 5 g micronized itraconazole are combined with 64 g PCCA LOXASPERSE base and mixed and encapsulated according to the procedure of Example 1. 1.03 g vancomycin hydrochloride equals 1 g vancomycin. Each capsule contains approximately 0.015 g fluticasone, 0.05 g itraconazole and 0.64 g LOXASPERSE.

Example 18

Preparation of a Dry Formulation of 0.3% Montelukast, 1.5% Fluticasone, 0.2% Levocetirizine Dihydrochloride 0.3 g montelukast sodium, 0.2 g levocetirizine dihydrochloride and 1.5 g fluticasone 20% aliquot are combined with 68.7 g PCCA LOXASPERSE base and mixed and encapsulated according to the procedure of Example 1. Each capsule contains approximately 0.003 g montelukast sodium, 0.002 g levocetirizine dihydrochloride 0.015 g fluticasone, and 0.64 g LOXASPERSE.

Example 19

Preparation of a Dry Formulation of 5.15% Vancomycin Hydrochloride, 20% Mupirocin 5.15 g vancomycin hydrochloride and 20 g mupirocin are combined with PCCA LOXASPERSE base and mixed and encapsulated according to the procedure of Example 1 are combined, mixed and encapsulated according to the procedure of Example 1. Each capsule contains approximately 0.0515 g vancomycin hydrochloride and 0.2 g mupirocin.

Example 20

Preparation of a Dry Formulation of 20% Mupirocin 20 g mupirocin is combined with 12.92 g PCCA LOXASPERSE base and mixed and encapsulated according to the procedure of Example 1 The sodium phosphate dibasic powder is ground prior to mixing with the rest of the ingredients. Each capsule contains approximately 0.2 g mupirocin.

Example 21

Preparation of a Dry Formulation of 15% Colistimethate Sodium 15 g colistimethate sodium is combined with 27 g PCCA LOXASPERSE base and mixed and encapsulated according to the procedure of Example 1 Each capsule contains approximately 0.15 g colistimethate sodium. The capsules should be stored under refrigeration.

What is claimed is:

1. A dry powder or capsule formulation suitable for mixing with liquid immediately prior to administration, the dry formulation comprising the following actives in combination with pharmaceutically acceptable excipients or additives:
   a) antibiotics comprising at least sulfamethoxazole and trimethoprim;
   b) one or more anti-inflammatory steroids comprising at least fluticasone; and
   c) one or more antifungal agents comprising at least one antifungal agent selected from the group consisting of fluconazole, itraconazole, amphotericin B, voriconazole and nystatin.

2. The dry formulation of claim 1, wherein the dry formulation does not contain an antihistamine.

3. The dry formulation of claim 1, comprising 0.08 g sulfamethoxazole, 0.05 g trimethoprim, 0.015 g fluticasone, and 0.015 g fluconazole.

4. A method of preparing an orally administrable formulation comprising forming the dry formulation of claim 1 into an oral rinse or an oral solution by mixing the dry formulation with liquid.

5. An orally administrable formulation obtained by the method of claim 4.

6. A method for treating inflammatory, ulcerative and painful conditions of mucosal surfaces of the upper alimentary canal of a mammal comprising administering to a patient the orally administrable formulation of claim 5.

7. The method of claim 6, wherein the orally administrable formulation is an oral rinse and wherein the method comprises:
   (1) swishing the oral rinse formulation; and
   (2) expectorating the oral rinse formulation.

8. The method of claim 6, wherein the orally administrable formulation is an oral solution and wherein the method comprises:
   (1) swishing the oral solution; and
   (2) swallowing the oral solution.

9. The dry formulation according to claim 1, further comprising one or more of the following actives in combination with pharmaceutically acceptable excipients or additives:
   a) at least one leukotriene receptor antagonist; and
   b) at least one non-sedative antihistamine.

10. A method of preparing a formulation for aural administration comprising forming the dry formulation of claim 9 into a solution or suspension with a diluent suitable for otic delivery of active ingredients.

11. A formulation for aural administration obtained by the method of claim 10.

12. A method for treating inflammatory, ulcerative and painful conditions of the ear of a mammal comprising administering to said mammal the formulation for aural administration of claim 11.

13. The method of claim 12, wherein the formulation for aural administration is administered by instillation of the solution or suspension into the ear canal.

14. The method of claim 12, wherein the administering step is carried out three times a day.

15. The method of claim 12, wherein the condition is selected from the group consisting of:
   otitis externa, otitis media, otorrhea, acute mastoiditis, otosclerosis, otic pain, otic bleeding, otic inflammation, Lermoyez's syndrome, Meniere's disease, vestibular neuronitis, benign paroxysmal positional vertigo, herpes zoster oticus, Ramsay Hunt's syndrome, viral neuronitis, ganglionitis, geniculate herpes, labyrinthitis, purulent labyrinthitis, perilymph fistulas, presbycusis, drug-induced ototoxicity, acoustic neuromas, aerotitis media, infectious myringitis, bullous myringitis, squamous cell carcinoma, basal cell carcinoma, precancerous otic conditions, nonchromaffin paragangliomas, chemodectomas, glomus jugulare tumors, glomus tympanicum tumors, perichondritis, aural eczematoid dermatitis, malignant external otitis, subperichondrial hematoma, ceruminomas, impacted cerumen, sebaceous cysts, osteomas, keloids, otalgia, tinnitus, vertigo, tympanic membrane infection, tympanitis, otic furuncles, petrositis, conductive and sensorineural hearing loss, epidural abscess, lateral sinus thrombosis, subdural empyema, otitic hydrocephalus, Dandy's syndrome, bullous myringitis, diffuse external otitis, foreign bodies, keratosis obturans, otic neoplasm, otomycosis, trauma, acute barotitis media, acute eustachian tube obstruction, postsurgical otalgia, cholesteatoma, and infections related to an otic surgical procedure.

16. The dry formulation of claim 1, comprising 1 mg to 100 mg sulfamethoxazole, 1 mg to 50 mg trimethoprim, 1 mg to 5 mg fluticasone, and 1 mg to 50 mg fluconazole.

* * * * *